United States Patent
Magnuson et al.

(10) Patent No.: US 8,152,831 B2
(45) Date of Patent: Apr. 10, 2012

(54) FOAM EMBOLIC PROTECTION DEVICE

(75) Inventors: Mark A. Magnuson, Bloomington, IN (US); Fred T. Parker, Unionville, IN (US)

(73) Assignee: Cook Medical Technologies LLC, Bloomington, IN (US)

(\*) Notice: Subject to any disclaimer, the term of this patent is extended or adjusted under 35 U.S.C. 154(b) by 1119 days.

(21) Appl. No.: 11/600,571

(22) Filed: Nov. 16, 2006

(65) Prior Publication Data

US 2007/0118173 A1    May 24, 2007

Related U.S. Application Data

(60) Provisional application No. 60/737,480, filed on Nov. 17, 2005.

(51) Int. Cl.
*A61M 29/00* (2006.01)
(52) U.S. Cl. ........................................... 606/200
(58) Field of Classification Search ............... 623/23.73; 606/200, 127, 213
See application file for complete search history.

(56) References Cited

U.S. PATENT DOCUMENTS

| | | | |
|---|---|---|---|
| 3,108,593 A | 10/1963 | Glassman | |
| 3,334,629 A | 8/1967 | Cohn | |
| 3,472,230 A * | 10/1969 | Fogarty | 606/127 |
| 3,547,103 A | 12/1970 | Cook | |
| 3,635,223 A | 1/1972 | Klieman | |
| 3,923,065 A | 12/1975 | Nozick et al. | |
| 3,952,747 A | 4/1976 | Kimmell, Jr. | |
| 3,978,863 A | 9/1976 | Fettel et al. | |
| 3,996,938 A | 12/1976 | Clark, III | |
| 4,425,908 A | 1/1984 | Simon | |
| 4,456,000 A | 6/1984 | Schjeldahl et al. | |
| 4,494,531 A | 1/1985 | Gianturco | |
| 4,548,206 A | 10/1985 | Osborne | |
| 4,561,439 A | 12/1985 | Bishop et al. | |
| 4,562,039 A * | 12/1985 | Koehler | 419/2 |
| 4,604,094 A | 8/1986 | Shook | |
| 4,619,246 A | 10/1986 | Molgaard-Nielsen et al. | |
| 4,643,184 A | 2/1987 | Mobin-Uddin | |

(Continued)

FOREIGN PATENT DOCUMENTS

DE    3429850 A1    2/1986

(Continued)

OTHER PUBLICATIONS

Journal= Appl. Phys. Lett. 82, 2727 (2003); Title = Low-density open-cell foams in the NiTi system Authors= David S. Grummon, John A. Shaw, and Antoine Gremillet (accepted Feb. 24, 2003) Journal= Appl. Phys. Lett. 82, 2727 (2003); (3 pages).*

(Continued)

*Primary Examiner* — Melanie Tyson
*Assistant Examiner* — Son Dang
(74) *Attorney, Agent, or Firm* — Brinks Hofer Gilson & Lione

(57) ABSTRACT

An embolic protection device includes a foam body attached to a plurality of flexible struts. The foam body has a generally conical geometry and the bottom of the conical geometry having a generally conical recess. The filter portion has pores sized such that blood cells can pass through the foam body, but larger material such as objects would be trapped in the recess. Each strut is attached along the periphery of the foam body and extend from the first end of the foam body to a connection point located proximate the first end.

16 Claims, 8 Drawing Sheets

FIG. 2

U.S. PATENT DOCUMENTS

| | | | |
|---|---|---|---|
| 4,646,736 A | 3/1987 | Auth | |
| 4,650,472 A | 3/1987 | Bates | |
| 4,665,906 A | 5/1987 | Jervis | |
| 4,669,464 A | 6/1987 | Sulepov | |
| 4,688,553 A | 8/1987 | Metals | |
| 4,723,549 A | 2/1988 | Wholey et al. | |
| 4,727,873 A | 3/1988 | Mobin-Uddin | |
| 4,732,152 A | 3/1988 | Wallsten et al. | |
| 4,817,600 A | 4/1989 | Herms et al. | |
| 4,824,435 A | 4/1989 | Giesy et al. | |
| 4,832,055 A | 5/1989 | Palestrant | |
| 4,846,794 A | 7/1989 | Hertzer | |
| 4,848,343 A | 7/1989 | Wallsten et al. | |
| 4,873,978 A | 10/1989 | Ginsburg | |
| 4,943,297 A | 7/1990 | Saveliev et al. | |
| 4,957,501 A | 9/1990 | Lahille et al. | |
| 4,990,156 A | 2/1991 | Lefebvre | |
| 4,998,916 A | 3/1991 | Hammerslag et al. | |
| 5,053,008 A | 10/1991 | Bajaj | |
| 5,059,205 A | 10/1991 | El-Nounou et al. | |
| 5,069,226 A | 12/1991 | Yamauchi et al. | |
| 5,078,726 A | 1/1992 | Kreamer | |
| 5,100,423 A | 3/1992 | Fearnot | |
| 5,108,418 A | 4/1992 | Lefebvre | |
| 5,108,419 A | 4/1992 | Reger et al. | |
| 5,112,347 A | 5/1992 | Taheri | |
| 5,129,890 A | 7/1992 | Bates et al. | |
| 5,133,733 A | 7/1992 | Rasmussen et al. | |
| 5,147,379 A | 9/1992 | Sabbaghian et al. | |
| 5,152,777 A | 10/1992 | Goldberg | |
| 5,160,342 A | 11/1992 | Reger et al. | |
| 5,163,927 A | 11/1992 | Woker et al. | |
| 5,203,772 A | 4/1993 | Hammerslag et al. | |
| 5,234,458 A | 8/1993 | Metais | |
| 5,242,462 A | 9/1993 | El-Nounou | |
| 5,243,996 A | 9/1993 | Hall | |
| 5,251,640 A | 10/1993 | Osborne | |
| 5,263,964 A | 11/1993 | Purdy | |
| 5,300,086 A | 4/1994 | Gory et al. | |
| 5,324,304 A | 6/1994 | Rasmussen | |
| 5,329,942 A | 7/1994 | Gunther et al. | |
| 5,344,427 A | 9/1994 | Cottenceau et al. | |
| 5,350,397 A | 9/1994 | Palermo et al. | |
| 5,350,398 A | 9/1994 | Pavcnik et al. | |
| 5,364,345 A | 11/1994 | Lowery et al. | |
| 5,370,657 A | 12/1994 | Irie | |
| 5,375,612 A | 12/1994 | Cottenceau et al. | |
| 5,383,887 A | 1/1995 | Nadal | |
| 5,413,586 A | 5/1995 | Dibie et al. | |
| 5,415,630 A | 5/1995 | Gory et al. | |
| 5,417,708 A | 5/1995 | Hall et al. | |
| 5,451,233 A | 9/1995 | Yock | |
| 5,458,573 A | 10/1995 | Summers | |
| 5,522,881 A | 6/1996 | Lentz | |
| 5,527,338 A | 6/1996 | Purdy | |
| 5,531,788 A | 7/1996 | Dibie et al. | |
| 5,549,551 A | 8/1996 | Peacock et al. | |
| 5,549,626 A | 8/1996 | Miller et al. | |
| 5,556,414 A | 9/1996 | Turi | |
| 5,562,698 A | 10/1996 | Parker | |
| 5,571,135 A | 11/1996 | Fraser et al. | |
| 5,591,195 A | 1/1997 | Taheri et al. | |
| 5,601,595 A | 2/1997 | Smith | |
| 5,624,461 A | 4/1997 | Mariant | |
| 5,626,605 A | 5/1997 | Irie et al. | |
| 5,630,797 A | 5/1997 | Diedrich et al. | |
| 5,634,942 A | 6/1997 | Chevillon et al. | |
| 5,649,953 A | 7/1997 | Lefebvre | |
| 5,662,703 A | 9/1997 | Yurek et al. | |
| 5,669,933 A | 9/1997 | Simon et al. | |
| 5,681,347 A | 10/1997 | Cathcart et al. | |
| 5,690,642 A | 11/1997 | Osborne et al. | |
| 5,690,667 A | 11/1997 | Gia | |
| 5,693,067 A | 12/1997 | Purdy | |
| 5,693,087 A | 12/1997 | Parodi | |
| 5,695,518 A | 12/1997 | Laerum | |
| 5,695,519 A | 12/1997 | Summers et al. | |
| 5,700,253 A | 12/1997 | Parker | |
| 5,709,704 A | 1/1998 | Nott et al. | |
| 5,713,853 A | 2/1998 | Clark et al. | |
| 5,720,764 A | 2/1998 | Naderlinger | |
| 5,725,550 A | 3/1998 | Nadal | |
| 5,738,667 A | 4/1998 | Solar | |
| 5,746,767 A | 5/1998 | Smith | |
| 5,755,772 A | 5/1998 | Evans et al. | |
| 5,755,790 A | 5/1998 | Chevillon et al. | |
| 5,766,203 A | 6/1998 | Imran et al. | |
| 5,769,816 A | 6/1998 | Barbut et al. | |
| 5,769,871 A | 6/1998 | Mers et al. | |
| 5,795,322 A | 8/1998 | Boudewijn | |
| 5,800,457 A | 9/1998 | Gelbfish et al. | |
| 5,800,525 A | 9/1998 | Bachinski et al. | |
| 5,810,874 A | 9/1998 | Lefebvre | |
| 5,814,027 A | 9/1998 | Hassett et al. | |
| 5,814,064 A | 9/1998 | Daniel et al. | |
| 5,820,592 A | 10/1998 | Hammerslag | |
| 5,827,324 A | 10/1998 | Cassell et al. | |
| 5,830,230 A | 11/1998 | Berryman et al. | |
| 5,836,968 A | 11/1998 | Simon et al. | |
| 5,836,969 A | 11/1998 | Kim et al. | |
| 5,846,260 A | 12/1998 | Maahs | |
| 5,853,420 A | 12/1998 | Chevillon et al. | |
| 5,876,367 A | 3/1999 | Kaganov et al. | |
| 5,893,869 A | 4/1999 | Barnhart et al. | |
| 5,895,391 A | 4/1999 | Farnholtz | |
| 5,895,399 A | 4/1999 | Barbut et al. | |
| 5,895,410 A | 4/1999 | Forber et al. | |
| 5,908,435 A | 6/1999 | Samuels | |
| 5,910,154 A * | 6/1999 | Tsugita et al. | 606/200 |
| 5,911,702 A | 6/1999 | Romley et al. | |
| 5,911,704 A | 6/1999 | Humes | |
| 5,911,717 A | 6/1999 | Jacobsen et al. | |
| 5,911,734 A | 6/1999 | Tsugita et al. | |
| 5,919,224 A | 7/1999 | Thompson et al. | |
| 5,925,062 A | 7/1999 | Purdy | |
| 5,925,063 A | 7/1999 | Khosravi | |
| 5,928,260 A | 7/1999 | Chin et al. | |
| 5,928,261 A | 7/1999 | Ruiz | |
| 5,938,683 A | 8/1999 | Lefebvre | |
| 5,941,896 A | 8/1999 | Kerr | |
| 5,944,728 A | 8/1999 | Bates | |
| 5,947,985 A | 9/1999 | Imran | |
| 5,947,995 A | 9/1999 | Samuels | |
| 5,948,017 A | 9/1999 | Taheri | |
| 5,951,567 A | 9/1999 | Javier, Jr. et al. | |
| 5,954,741 A | 9/1999 | Fox | |
| 5,954,742 A | 9/1999 | Osypka | |
| 5,954,745 A | 9/1999 | Gertler et al. | |
| 5,968,057 A | 10/1999 | Taheri | |
| 5,968,071 A | 10/1999 | Chevillon et al. | |
| 5,972,019 A | 10/1999 | Engelson et al. | |
| 5,976,162 A | 11/1999 | Doan et al. | |
| 5,976,172 A | 11/1999 | Homsma et al. | |
| 5,980,555 A | 11/1999 | Barbut et al. | |
| 5,984,947 A | 11/1999 | Smith | |
| 5,984,965 A | 11/1999 | Knapp et al. | |
| 5,989,281 A | 11/1999 | Barbut et al. | |
| 6,001,118 A | 12/1999 | Daniel et al. | |
| 6,007,557 A | 12/1999 | Ambrisco et al. | |
| 6,007,558 A | 12/1999 | Ravenscroft et al. | |
| 6,010,522 A | 1/2000 | Barbut et al. | |
| 6,013,093 A | 1/2000 | Nott et al. | |
| 6,015,424 A | 1/2000 | Rosenbluth et al. | |
| 6,027,520 A | 2/2000 | Tsugita et al. | |
| 6,036,717 A | 3/2000 | Mers Kelly et al. | |
| 6,036,720 A | 3/2000 | Abrams et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,745 A | 5/2000 | Gelbfish | |
| 6,059,813 A | 5/2000 | Vrba et al. | |
| 6,059,814 A | 5/2000 | Ladd | |
| 6,063,113 A | 5/2000 | Kavteladze et al. | |
| 6,066,158 A | 5/2000 | Engelson et al. | |
| 6,068,645 A | 5/2000 | Tu | |
| 6,074,357 A | 6/2000 | Kaganov et al. | |

| Patent Number | Date | Inventor(s) |
|---|---|---|
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,096,070 A | 8/2000 | Ragheb et al. |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |
| 6,152,946 A | 11/2000 | Broome et al. |
| 6,152,947 A | 11/2000 | Ambrisco et al. |
| 6,156,061 A | 12/2000 | Wallace et al. |
| 6,156,062 A | 12/2000 | McGuinness |
| 6,159,230 A | 12/2000 | Samuels |
| 6,165,179 A | 12/2000 | Cathcart et al. |
| 6,165,198 A | 12/2000 | McGurk et al. |
| 6,165,199 A | 12/2000 | Barbut |
| 6,165,200 A | 12/2000 | Tsugita et al. |
| 6,168,579 B1 | 1/2001 | Tsugita et al. |
| 6,168,603 B1 | 1/2001 | Leslie et al. |
| 6,168,610 B1 | 1/2001 | Marin et al. |
| 6,168,622 B1 | 1/2001 | Mazzocchi |
| 6,171,327 B1 | 1/2001 | Daniel et al. |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,193,739 B1 | 2/2001 | Chevillon et al. |
| 6,203,561 B1 | 3/2001 | Ramee et al. |
| 6,206,931 B1 | 3/2001 | Cook et al. |
| 6,214,025 B1 | 4/2001 | Thistle et al. |
| 6,214,026 B1 | 4/2001 | Lepak et al. |
| 6,221,091 B1 | 4/2001 | Khosravi |
| 6,224,620 B1 | 5/2001 | Maahs |
| 6,231,588 B1 | 5/2001 | Zadno-Azizi |
| 6,231,589 B1 | 5/2001 | Wessman et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,092 B1 | 6/2001 | Qin et al. |
| 6,251,122 B1 | 6/2001 | Tsukernik |
| 6,254,550 B1 | 7/2001 | McNamara et al. |
| 6,254,633 B1 | 7/2001 | Pinchuk et al. |
| 6,258,026 B1 | 7/2001 | Ravenscroft et al. |
| 6,258,115 B1 | 7/2001 | Dubrul |
| 6,258,120 B1 | 7/2001 | McKenzie et al. |
| 6,261,305 B1 | 7/2001 | Marotta et al. |
| 6,264,672 B1 | 7/2001 | Fisher |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,277,125 B1 | 8/2001 | Barry et al. |
| 6,277,126 B1 | 8/2001 | Barry et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,710 B1 | 9/2001 | Cryer et al. |
| 6,299,604 B1 | 10/2001 | Ragheb et al. |
| 6,306,163 B1 | 10/2001 | Fitz |
| 6,309,399 B1 | 10/2001 | Barbut et al. |
| 6,312,444 B1 | 11/2001 | Barbut |
| 6,319,268 B1 | 11/2001 | Ambrisco et al. |
| 6,325,815 B1 | 12/2001 | Kusleika et al. |
| 6,325,816 B1 | 12/2001 | Fulton, III et al. |
| 6,328,755 B1 | 12/2001 | Marshall |
| 6,331,183 B1 | 12/2001 | Suon |
| 6,331,184 B1 | 12/2001 | Abrams |
| 6,334,864 B1 | 1/2002 | Amplatz et al. |
| 6,336,934 B1 | 1/2002 | Gilson et al. |
| 6,338,739 B1 | 1/2002 | Datta et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,048 B1 | 2/2002 | Chin et al. |
| 6,344,049 B1 | 2/2002 | Levinson et al. |
| 6,346,116 B1 | 2/2002 | Brooks et al. |
| 6,348,041 B1 | 2/2002 | Klint |
| 6,348,063 B1 | 2/2002 | Yassour et al. |
| 6,350,271 B1 | 2/2002 | Kurz et al. |
| 6,355,051 B1 | 3/2002 | Sisskind et al. |
| 6,358,228 B1 | 3/2002 | Tubman et al. |
| 6,361,545 B1 * | 3/2002 | Macoviak et al. ............ 606/200 |
| 6,361,546 B1 | 3/2002 | Khosravi |
| 6,361,547 B1 | 3/2002 | Hieshima |
| 6,364,895 B1 | 4/2002 | Greenhalgh |
| 6,364,896 B1 | 4/2002 | Addis |
| 6,368,338 B1 | 4/2002 | Konya et al. |
| 6,371,961 B1 | 4/2002 | Osborne et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,379,374 B1 | 4/2002 | Hieshima et al. |
| 6,380,457 B1 | 4/2002 | Yurek et al. |
| 6,383,146 B1 | 5/2002 | Klint |
| 6,383,171 B1 | 5/2002 | Gifford et al. |
| 6,383,174 B1 | 5/2002 | Eder |
| 6,383,193 B1 | 5/2002 | Cathcart et al. |
| 6,383,196 B1 | 5/2002 | Leslie et al. |
| 6,383,205 B1 | 5/2002 | Samson et al. |
| 6,383,206 B1 | 5/2002 | Gillick et al. |
| 6,391,044 B1 * | 5/2002 | Yadav et al. ................. 606/200 |
| 6,391,045 B1 | 5/2002 | Kim et al. |
| 6,391,052 B2 | 5/2002 | Buirge et al. |
| 6,395,014 B1 | 5/2002 | Macoviak et al. |
| 6,402,771 B1 | 6/2002 | Palmer et al. |
| 6,402,772 B1 | 6/2002 | Amplatz et al. |
| 6,409,742 B1 | 6/2002 | Fulton, III et al. |
| 6,413,235 B1 | 7/2002 | Parodi |
| 6,416,530 B2 | 7/2002 | DeVries et al. |
| 6,419,686 B1 | 7/2002 | McLeod et al. |
| 6,423,052 B1 | 7/2002 | Escano |
| 6,423,086 B1 | 7/2002 | Barbut et al. |
| 6,425,909 B1 | 7/2002 | Dieck et al. |
| 6,428,557 B1 | 8/2002 | Hilaire |
| 6,428,558 B1 | 8/2002 | Jones et al. |
| 6,428,559 B1 | 8/2002 | Johnson |
| 6,432,122 B1 | 8/2002 | Gilson et al. |
| 6,436,112 B2 | 8/2002 | Wensel et al. |
| 6,436,120 B1 | 8/2002 | Meglin |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,454,775 B1 | 9/2002 | Demarais et al. |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B1 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Don Michael et al. |
| 6,491,712 B1 | 12/2002 | O'Connor |
| 6,494,895 B2 | 12/2002 | Addis |

| | | |
|---|---|---|
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B1 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,520,983 B1 | 2/2003 | Colgan et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,770 B1 | 3/2003 | Lepulu et al. |
| 6,533,800 B1 | 3/2003 | Barbut |
| 6,537,293 B1 | 3/2003 | Berryman et al. |
| 6,537,294 B1 | 3/2003 | Boyle et al. |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 | 4/2003 | Shen et al. |
| 6,554,849 B1 | 4/2003 | Jones et al. |
| 6,558,404 B2 | 5/2003 | Tsukernik |
| 6,558,405 B1 * | 5/2003 | McInnes .................. 606/200 |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,227 B2 | 7/2003 | Klint |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,592,616 B1 | 7/2003 | Stack et al. |
| 6,595,983 B2 | 7/2003 | Voda |
| 6,596,011 B2 | 7/2003 | Johnson et al. |
| 6,599,275 B1 | 7/2003 | Fischer, Jr. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,602,280 B2 | 8/2003 | Chobotov |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,611,720 B2 | 8/2003 | Hata et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B1 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Evans et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,160 B1 | 11/2003 | Heesch |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,676,682 B1 | 1/2004 | Tsugita et al. |
| 6,679,902 B1 | 1/2004 | Boyle et al. |
| 6,689,144 B2 | 2/2004 | Gerberding |
| 6,695,813 B1 | 2/2004 | Boyle et al. |
| 6,695,865 B2 | 2/2004 | Boyle et al. |
| 6,702,834 B1 | 3/2004 | Boylan et al. |
| 6,709,450 B2 | 3/2004 | Kang et al. |
| 6,712,835 B2 | 3/2004 | Mazzocchi et al. |
| 6,716,207 B2 | 4/2004 | Farnholtz |
| 6,716,231 B1 | 4/2004 | Rafiee et al. |
| 6,726,701 B2 | 4/2004 | Gilson et al. |
| 6,730,064 B2 | 5/2004 | Ragheb et al. |
| 6,755,856 B2 | 6/2004 | Fierens et al. |
| 6,758,855 B2 | 7/2004 | Fulton, III et al. |
| 6,761,727 B1 | 7/2004 | Ladd |
| 6,773,446 B1 | 8/2004 | Dwyer et al. |
| 6,773,448 B2 | 8/2004 | Kusleika et al. |
| 6,774,278 B1 | 8/2004 | Ragheb et al. |
| 6,780,175 B1 | 8/2004 | Sachdeva et al. |
| 6,793,667 B2 | 9/2004 | Hebert et al. |
| 6,793,668 B1 | 9/2004 | Fisher |
| 6,833,002 B2 | 12/2004 | Stack et al. |
| 6,855,154 B2 | 2/2005 | Abdel-Gawwad |
| 6,866,677 B2 | 3/2005 | Douk et al. |
| 6,866,680 B2 | 3/2005 | Yassour et al. |
| 6,872,211 B2 | 3/2005 | White et al. |
| 6,878,153 B2 | 4/2005 | Linder et al. |
| 6,896,691 B2 | 5/2005 | Boylan et al. |
| 6,929,709 B2 | 8/2005 | Smith |
| 6,932,831 B2 | 8/2005 | Forber |
| 6,939,361 B1 | 9/2005 | Kleshinski |
| 6,942,682 B2 | 9/2005 | Vrba et al. |
| 6,955,685 B2 | 10/2005 | Escamilla et al. |
| 6,964,670 B1 | 11/2005 | Shah et al. |
| 6,964,674 B1 | 11/2005 | Matsuura et al. |
| 6,969,396 B2 | 11/2005 | Krolik et al. |
| 6,974,469 B2 | 12/2005 | Broome et al. |
| 6,974,473 B2 | 12/2005 | Barclay et al. |
| 6,986,784 B1 | 1/2006 | Weiser et al. |
| 6,991,641 B2 | 1/2006 | Diaz et al. |
| 7,128,073 B1 | 10/2006 | Van Der Burg et al. |
| 7,166,120 B2 | 1/2007 | Kusleika |
| 7,174,636 B2 | 2/2007 | Lowe |
| 7,189,249 B2 | 3/2007 | Hart et al. |

| | | |
|---|---|---|
| 7,255,687 B2 | 8/2007 | Huang et al. |
| 7,285,130 B2 | 10/2007 | Austin |
| 7,306,619 B1 | 12/2007 | Palmer |
| 7,371,248 B2 | 5/2008 | Dapolito et al. |
| 7,393,358 B2 | 7/2008 | Malewicz |
| 7,604,649 B2 | 10/2009 | McGuckin et al. |
| 7,666,216 B2 | 2/2010 | Hogendijk et al. |
| 7,731,722 B2 | 6/2010 | Lavelle et al. |
| 7,766,934 B2 | 8/2010 | Pal et al. |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0041928 A1 | 11/2001 | Pavcnik et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002383 A1 | 1/2002 | Sepetka et al. |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099405 A1 | 7/2002 | Yurek et al. |
| 2002/0099407 A1 | 7/2002 | Becker et al. |
| 2002/0099435 A1 | 7/2002 | Stinson |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0165598 A1 | 11/2002 | Wahr et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0177899 A1* | 11/2002 | Eum et al. .................... 623/23.7 |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004537 A1 | 1/2003 | Boyle et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucek |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1 | 3/2003 | Harrison et al. |
| 2003/0050662 A1 | 3/2003 | Don Michael |

| | | | | | | |
|---|---|---|---|---|---|---|
| 2003/0055452 A1* | 3/2003 | Joergensen et al. ............ 606/200 | | 2003/0181943 A1 | 9/2003 | Daniel et al. |
| 2003/0055480 A1 | 3/2003 | Fischell et al. | | 2003/0717769 | 9/2003 | Barbut |
| 2003/0060843 A1 | 3/2003 | Boucher | | 2003/0187474 A1 | 10/2003 | Keegan et al. |
| 2003/0060844 A1 | 3/2003 | Borillo et al. | | 2003/0187475 A1 | 10/2003 | Tsugita et al. |
| 2003/0065354 A1 | 4/2003 | Boyle et al. | | 2003/0187495 A1 | 10/2003 | Cully et al. |
| 2003/0065355 A1 | 4/2003 | Weber | | 2003/0191492 A1 | 10/2003 | Gellman et al. |
| 2003/0065356 A1 | 4/2003 | Tsugita et al. | | 2003/0191493 A1 | 10/2003 | Epstein et al. |
| 2003/0069596 A1 | 4/2003 | Eskuri | | 2003/0195554 A1 | 10/2003 | Shen et al. |
| 2003/0073979 A1 | 4/2003 | Naimark et al. | | 2003/0195555 A1 | 10/2003 | Khairkhahan et al. |
| 2003/0074019 A1 | 4/2003 | Gray et al. | | 2003/0195556 A1 | 10/2003 | Stack et al. |
| 2003/0074054 A1 | 4/2003 | Duerig et al. | | 2003/0199819 A1 | 10/2003 | Beck |
| 2003/0078614 A1 | 4/2003 | Salahieh et al. | | 2003/0199917 A1 | 10/2003 | Knudson et al. |
| 2003/0083608 A1 | 5/2003 | Evans et al. | | 2003/0199918 A1 | 10/2003 | Patel et al. |
| 2003/0083692 A1 | 5/2003 | Vrba et al. | | 2003/0199919 A1 | 10/2003 | Palmer et al. |
| 2003/0083693 A1 | 5/2003 | Daniel et al. | | 2003/0199920 A1 | 10/2003 | Boylan et al. |
| 2003/0088211 A1 | 5/2003 | Anderson et al. | | 2003/0199921 A1 | 10/2003 | Palmer et al. |
| 2003/0088266 A1 | 5/2003 | Bowlin | | 2003/0204168 A1 | 10/2003 | Bosma et al. |
| 2003/0093110 A1 | 5/2003 | Vale | | 2003/0204202 A1 | 10/2003 | Palmer et al. |
| 2003/0093112 A1 | 5/2003 | Addis | | 2003/0204203 A1 | 10/2003 | Khairkhahan et al. |
| 2003/0097094 A1 | 5/2003 | Ouriel et al. | | 2003/0208222 A1 | 11/2003 | Zadno-Azizi |
| 2003/0097145 A1 | 5/2003 | Goldberg et al. | | 2003/0208224 A1 | 11/2003 | Broome |
| 2003/0100917 A1 | 5/2003 | Boyle et al. | | 2003/0208225 A1 | 11/2003 | Goll et al. |
| 2003/0100918 A1 | 5/2003 | Duane | | 2003/0208226 A1 | 11/2003 | Bruckheimer et al. |
| 2003/0100919 A1 | 5/2003 | Hopkins et al. | | 2003/0208227 A1 | 11/2003 | Thomas |
| 2003/0105472 A1 | 6/2003 | McAlister | | 2003/0208228 A1 | 11/2003 | Gilson et al. |
| 2003/0105484 A1 | 6/2003 | Boyle et al. | | 2003/0208229 A1 | 11/2003 | Kletschka |
| 2003/0105486 A1 | 6/2003 | Murphy et al. | | 2003/0208253 A1 | 11/2003 | Beyer et al. |
| 2003/0109824 A1 | 6/2003 | Anderson et al. | | 2003/0212428 A1 | 11/2003 | Richter |
| 2003/0109897 A1 | 6/2003 | Walak et al. | | 2003/0212429 A1 | 11/2003 | Keegan et al. |
| 2003/0109916 A1 | 6/2003 | Don Michael | | 2003/0212431 A1 | 11/2003 | Brady et al. |
| 2003/0114879 A1 | 6/2003 | Euteneuer et al. | | 2003/0212432 A1 | 11/2003 | Khairkhahan et al. |
| 2003/0114880 A1 | 6/2003 | Hansen et al. | | 2003/0212433 A1 | 11/2003 | Ambrisco et al. |
| 2003/0120303 A1 | 6/2003 | Boyle et al. | | 2003/0212434 A1 | 11/2003 | Thielen |
| 2003/0120304 A1 | 6/2003 | Kaganov et al. | | 2003/0216774 A1 | 11/2003 | Larson |
| 2003/0125764 A1 | 7/2003 | Brady et al. | | 2003/0220665 A1 | 11/2003 | Eskuri et al. |
| 2003/0125765 A1 | 7/2003 | Blackledge et al. | | 2003/0220667 A1 | 11/2003 | Van der Burg et al. |
| 2003/0130680 A1 | 7/2003 | Russell | | 2003/0225418 A1 | 12/2003 | Esksuri et al. |
| 2003/0130681 A1 | 7/2003 | Ungs | | 2003/0225435 A1 | 12/2003 | Huter et al. |
| 2003/0130682 A1 | 7/2003 | Broome et al. | | 2003/0229374 A1 | 12/2003 | Brady et al. |
| 2003/0130684 A1 | 7/2003 | Brady et al. | | 2003/0233117 A1 | 12/2003 | Adams et al. |
| 2003/0130685 A1 | 7/2003 | Daniel et al. | | 2004/0006364 A1 | 1/2004 | Ladd |
| 2003/0130686 A1 | 7/2003 | Daniel et al. | | 2004/0006365 A1 | 1/2004 | Brady et al. |
| 2003/0130687 A1 | 7/2003 | Daniel et al. | | 2004/0006370 A1 | 1/2004 | Tsugita |
| 2003/0130688 A1 | 7/2003 | Daniel et al. | | 2004/0015152 A1 | 1/2004 | Day |
| 2003/0135232 A1 | 7/2003 | Douk et al. | | 2004/0039412 A1 | 2/2004 | Isshiki et al. |
| 2003/0135233 A1 | 7/2003 | Bates et al. | | 2004/0225321 A1 | 2/2004 | Krolik et al. |
| 2003/0139764 A1 | 7/2003 | Levinson et al. | | 2004/0049226 A1 | 3/2004 | Keegan et al. |
| 2003/0139765 A1 | 7/2003 | Patel et al. | | 2004/0054394 A1 | 3/2004 | Lee |
| 2003/0144685 A1 | 7/2003 | Boyle et al. | | 2004/0054395 A1 | 3/2004 | Lee et al. |
| 2003/0144686 A1 | 7/2003 | Martinez et al. | | 2004/0059372 A1 | 3/2004 | Tsugita |
| 2003/0144687 A1 | 7/2003 | Brady et al. | | 2004/0064067 A1 | 4/2004 | Ward |
| 2003/0144688 A1 | 7/2003 | Brady et al. | | 2004/0064179 A1 | 4/2004 | Linder et al. |
| 2003/0144689 A1 | 7/2003 | Brady et al. | | 2004/0068271 A1 | 4/2004 | McAlister |
| 2003/0150821 A1 | 8/2003 | Bates et al. | | 2004/0078044 A1 | 4/2004 | Kear |
| 2003/0153935 A1 | 8/2003 | Mialhe | | 2004/0082962 A1 | 4/2004 | Demarais et al. |
| 2003/0153942 A1 | 8/2003 | Wang et al. | | 2004/0088038 A1* | 5/2004 | Dehnad et al. ............... 623/1.15 |
| 2003/0153943 A1 | 8/2003 | Michael et al. | | 2004/0093009 A1 | 5/2004 | Denison et al. |
| 2003/0153944 A1 | 8/2003 | Phung et al. | | 2004/0093012 A1 | 5/2004 | Cully et al. |
| 2003/0153945 A1 | 8/2003 | Patel et al. | | 2004/0093016 A1 | 5/2004 | Root et al. |
| 2003/0158518 A1 | 8/2003 | Schonholz et al. | | 2004/0093059 A1 | 5/2004 | Lee et al. |
| 2003/0158574 A1 | 8/2003 | Esch et al. | | 2004/0098022 A1 | 5/2004 | Barone |
| 2003/0158575 A1 | 8/2003 | Boylan et al. | | 2004/0098026 A1* | 5/2004 | Joergensen et al. ............ 606/200 |
| 2003/0163158 A1 | 8/2003 | White | | 2004/0098033 A1 | 5/2004 | Leeflang et al. |
| 2003/0163159 A1 | 8/2003 | Patel et al. | | 2004/0098112 A1 | 5/2004 | DiMatteo et al. |
| 2003/0167068 A1 | 9/2003 | Amplatz | | 2004/0102719 A1 | 5/2004 | Keith et al. |
| 2003/0167069 A1 | 9/2003 | Gonzales et al. | | 2004/0106944 A1 | 6/2004 | Daniel et al. |
| 2003/0171769 A1 | 9/2003 | Barbut | | 2004/0116831 A1 | 6/2004 | Vrba |
| 2003/0171770 A1 | 9/2003 | Kusleika et al. | | 2004/0133232 A1 | 7/2004 | Rosenbluth et al. |
| 2003/0171771 A1 | 9/2003 | Anderson et al. | | 2004/0138696 A1 | 7/2004 | Drasler et al. |
| 2003/0171772 A1 | 9/2003 | Amplatz | | 2004/0153118 A1 | 8/2004 | Clubb et al. |
| 2003/0171800 A1 | 9/2003 | Bicek et al. | | 2004/0158278 A1 | 8/2004 | Becker et al. |
| 2003/0171803 A1 | 9/2003 | Shimon | | 2004/0162576 A1 | 8/2004 | Barbut et al. |
| 2003/0176884 A1 | 9/2003 | Berrada et al. | | 2004/0164030 A1 | 8/2004 | Lowe et al. |
| 2003/0176885 A1 | 9/2003 | Broome et al. | | 2004/0167567 A1 | 8/2004 | Cano et al. |
| 2003/0176886 A1 | 9/2003 | Wholey et al. | | 2004/0176794 A1 | 9/2004 | Khosravi |
| 2003/0176887 A1 | 9/2003 | Petersen | | 2004/0176833 A1 | 9/2004 | Pavcnik et al. |
| 2003/0176888 A1 | 9/2003 | O'Connell | | 2004/0199203 A1 | 10/2004 | Oslund et al. |
| 2003/0176889 A1 | 9/2003 | Boyle et al. | | 2004/0204737 A1 | 10/2004 | Boismier et al. |
| 2003/0181942 A1 | 9/2003 | Sutton et al. | | 2004/0215322 A1 | 10/2004 | Kerr |

| | | |
|---|---|---|
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhaigh |
| 2005/0043743 A1 | 2/2005 | Dennis |
| 2005/0043756 A1* | 2/2005 | Lavelle et al. ............... 606/200 |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1* | 7/2005 | Jordan et al. ..................... 623/9 |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |
| 2006/0020334 A1* | 1/2006 | Lashinski et al. ............ 623/2.11 |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1127556 A2 | 8/2001 |
| EP | 1310219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

Rubicon Embolic Filter, The Next Generation of EM, Rubicon Medical, www.rubiconmed.com.
Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.

* cited by examiner

FOAM EMBOLIC PROTECTION DEVICE

CROSS-REFERENCE TO RELATED APPLICATIONS

This application claims the benefit of U.S. Provisional Application Ser. No. 60/737,480 filed on Nov. 17, 2005, entitled "FOAM EMBOLIC PROTECTION DEVICE", the entire contents of which are incorporated herein by reference.

BACKGROUND

1. Field of the Invention

The present invention generally relates to a medical device for embolic protection.

2. Description of Related Art

With the continuing advance of medical techniques, interventional procedures are more commonly being used to actively treat stenosis, occlusions, lesions, or other defects within a patient's blood vessels. Often the treated regions are in the coronary, carotid or even cerebral arteries. One procedure for treating an occluded or stenosed blood vessel is angioplasty. During angioplasty, an inflatable balloon is introduced into the occluded region. The balloon is inflated, pushing against the plaque or other material of the stenosed region and increasing the intralumenal diameter of the vessel. As the balloon presses against the material, portions of the material may inadvertently break free from the plaque deposit. These emboli may travel along the vessel and become trapped in a smaller blood vessel restricting blood flow to a vital organ, such as the brain.

Other methods for removing plaque or thrombus from arteries may include mechanical ablation, or non-contact ablation using light waves, sound waves, ultrasonics, or other radiation. Each of these methods are subject to the risk that some thrombogenic material may dislodge from the wall of the vessel and occlude a smaller blood vessel. The occlusion may cause damage to the patient, including an ischemic stroke in the cerebral arteries.

To prevent the risk of damage from emboli, many devices have been used to restrict the flow of emboli downstream from the stenosed area. One method includes inserting a balloon that may be expanded to occlude the flow of blood through the artery downstream of the stenosed area. An aspirating catheter may be located between the balloon and stenosed area and used to remove emboli that may be caused by the treatment. However, because the balloon completely blocks blood flow through the vessel, the vessel may be occluded only for short periods of time, limiting use of the procedure.

As an alternative to occluding flow through the blood vessel, various filtering devices have been proposed. Such devices typically have elements that form legs or a mesh that capture embolic material, but allow blood cells to flow between the elements. Capturing the emboli in the filter device prevents the material from being lodged downstream in a smaller blood vessel. The filter may then be removed along with the embolic material after the procedure has been performed and the risk from emboli has decreased.

Challenges also exist with filtering devices. Often it is desirable to deploy filter devices from the proximal side of a stenosis. Therefore, the profile of the filtering device should be smaller than the opening in the stenosed vessel. Further, the smaller the profile of the filtering device the less risk of dislodging emboli during deployment of the device. In addition, if the filter portion is not held against the inside of the vessel wall, there is a risk that embolic material may pass between the filter and the vessel wall. The filter portion should also be durable and firmly secured to the medical device, since any damage caused to the medical device during deployment increases the risk that emboli might breach the medical device.

In view of the above, it is apparent that there exists a need for an improved medical device for embolic protection.

SUMMARY

In satisfying the above need, as well as overcoming the enumerated drawbacks and other limitations of the related art, the present invention provides an improved medical device for embolic protection.

The embolic protection device includes a foam body attached to a plurality of flexible struts. The foam body has a generally conical geometry and the bottom of the conical geometry includes a generally conical recess. The filter portion has pores sized such that blood cells can pass through the foam body, but larger material such as emboli are trapped in the recess. Each strut is attached along the periphery of the foam body and extend from the first end of the foam body to a connection point located proximate the first end. The struts are attached to one another to form a cannula extending proximally from the filter portion.

The struts are biased into an expanded state such that the filter portion is forced against an inner wall of the vessel. The embolic protection device also includes a core wire extending between the first and second ends of the basket. The core wire may be moved relative to the struts forcing the basket into a collapsed state.

Folds are provided in the filter portion to facilitate insertion and removal of the medical device. The folds extend radially from the apex along the side of the conical shape. The folds form an accordion-like alternating pattern of periodically spaced inward and outward folds.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 3a is a side view of an embolic protection assembly for capturing emboli during treatment of a stenotic lesion in accordance with one embodiment of the present invention;

FIG. 3b is an exploded side view of the assembly in FIG. 3a;

DETAILED DESCRIPTION

Figure 1:
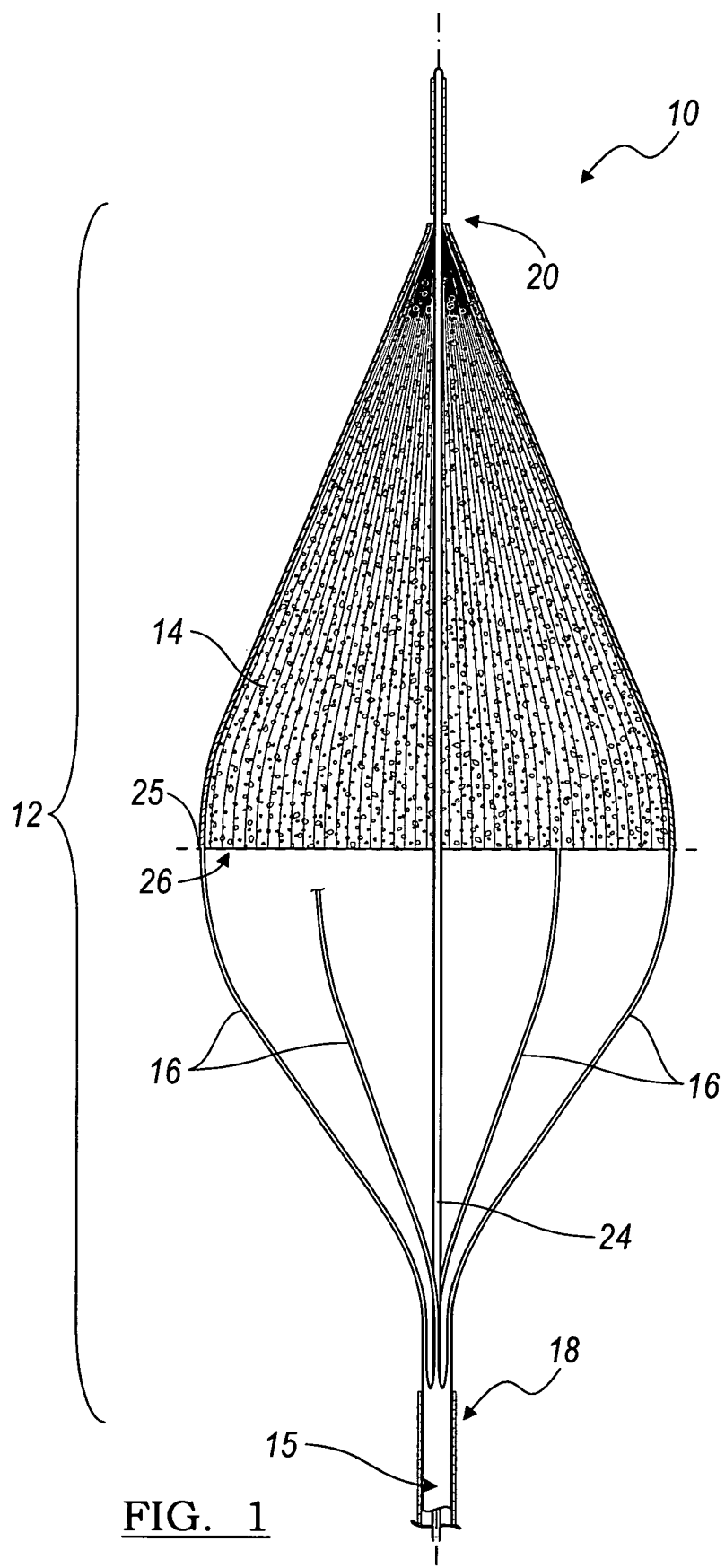
FIG. 1 is a side view of a medical device in accordance with the present invention.
Figure 2:
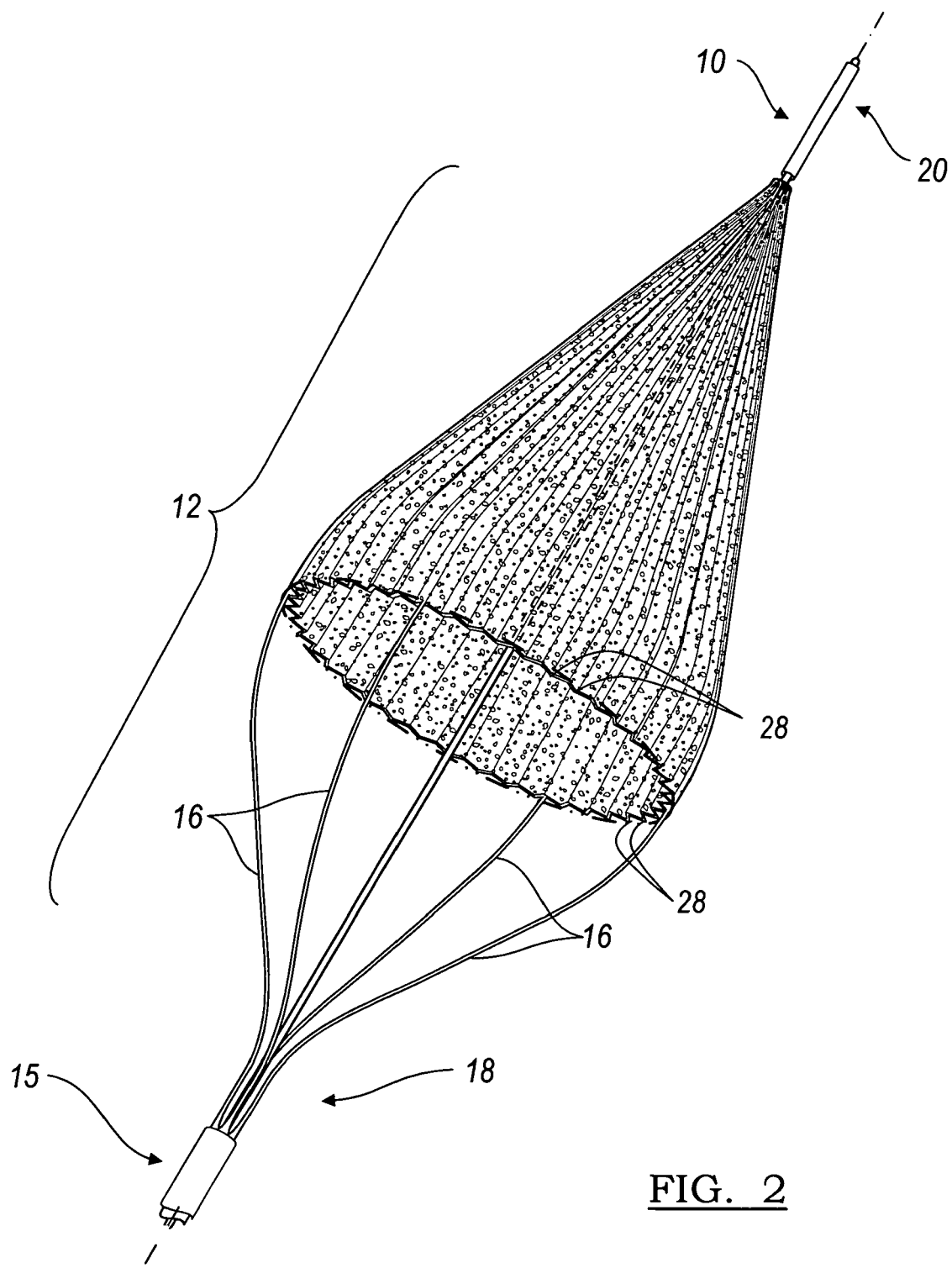
FIG. 2 is an perspective view of the medical device in FIG. 1.

Referring now to FIGS. 1 and 2, the medical device 10 includes a basket 12 formed from a filter portion 14 and a plurality of struts 16. The filter portion 14 has a foam body that forms a generally conical geometry. A conical recess 26 is provided in the bottom of the conical geometry allowing fluid and emboli to be contained within the recess 26. The opening 25 of recess 26 is enlarged when the basket 12 is in the expanded state for capturing emboli. As such, the opening 25 and recess 26 are configured to face toward the stenotic lesion. Accordingly, the filter portion 14 forms a proximally facing concave shape. The foam body is porous such that blood cells may be allowed to permeate and flow through the filter portion 14, while larger material such as emboli would be trapped within the recess 26. Accordingly, the size of the pores may be between about 80 and 100 micrometers, thereby allowing objects the size of blood cells to traverse through the pores.

The foam body may be made of any polymeric material, metal, shape memory alloy, mixtures thereof, or any suitable material to be used for capturing emboli from the stenotic lesion during treatment thereof without falling beyond the scope or spirit of the present invention. Preferably, the foam body is comprised of a shape memory material. More preferably, the foam body is comprised of a porous Nitinol foam. As described in more detail below, the super elastic and shape memory characteristics will facilitate the expansion and collapse of the filter portion 14 as the medical device 10 is deployed or retrieved.

A plurality of folds 28 are also formed in the filter portion 14. The folds 28 extend radially from the apex of the conical geometry and along the sides of the conical geometry. The folds 28 include a plurality of inward and outward folds in an alternating pattern. One example, of an alternating pattern of inward and outward folds is often illustrated by an accordion. The folds 28 minimize the profile of the foam body when it assumes the collapsed state. As previously discussed, minimizing the profile of the medical device 10 reduces the risk of dislodging emboli during insertion of the medical device 10.

The struts 16 are attached to the second end of the filter portion 14 and are radially spaced about the opening 25 in the bottom of the conical geometry. The struts 16 may be attached to the filter portion 14 by any suitable means, including but not limited to sonic bonding, thermal bonding, or adhesive bonding. The struts 16 extend proximally from the second end of the filter portion 14 and are attached to one another at a point proximate and concentrically aligned with the conical geometry. The struts 16 cooperate to form a tubular portion 15 that further extends proximally relative to the filter portion 14. A core wire 24 runs through the basket 12 and extends to the apex of the conical geometry. The tubular portion 15 includes a lumen that slidably engages the core wire 24. The struts 16 and core wire 24 may be used to facilitate the transition of the filter portion 14 between an expanded state and a collapsed state.

The struts 16 may be comprised of any suitable material, for example a superelastic material such as Nitinol, stainless steel wire, cobalt-chromium-nickel-molybdenum-iron alloy, or cobalt-chrome alloy. It is understood that the struts 16 may be formed of any other suitable material that will result in a self-opening or self-expanding basket, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its remembered state. The transition temperature is dependent on the relative proportions of the alloying elements Ni and Ti and the optional inclusion of alloying additives.

In one embodiment, the struts 16 and filter portion 14 are made from Nitinol with a transition temperature that is slightly below normal body temperature of humans, which is about 98.6° F. Although not necessarily a preferred embodiment, when the basket 12 is deployed in a body vessel and exposed to normal body temperature, the alloy of the struts 16 and filter portion 14 will transform to austenite, that is, the remembered state, which for one embodiment of the present invention is the expanded configuration when the basket 12 is deployed in the body vessel. To facilitate removal of the basket 12, the struts 16 and filter portion 14 are cooled to transform the material to martensite which is more ductile than austenite, making the struts 16 and filter portion 14 more malleable. As such, the basket 12 can be more easily collapsed and pulled into a lumen of a catheter for removal.

In another alternate embodiment, the struts 16 and filter portion 14 are made from Nitinol with a transition temperature that is above normal body temperature of humans, which is about 98.6° F. Although not necessarily a preferred embodiment, when the basket 12 is deployed in a body vessel and exposed to normal body temperature, the struts 16 and filter portion 14 are in the martensitic state so that the basket 12 is sufficiently ductile to bend or form into a desired shape, which for the present invention is an expanded configuration. To facilitate removal of the basket 12, the struts 16 and filter portion 14 are heated to transform the alloy to austenite so that the basket 12 becomes rigid and returns to a remembered state, which for the basket 12 of this alternate embodiment is a collapsed configuration.

In one embodiment of the medical device 10, the core wire 24 extends from the tubular portion 15 and is attached to the filter portion 14 at the apex of the conical geometry. The struts 16 and filter portion 14 are biased into an expanded state providing a radial force to support the filter portion 14 against an inner wall of the vessel. Accordingly, the core wire 24 may be moved distally relative to the struts 16, such that the struts 16 will be pulled tight against the core wire 24 causing the filter portion 14 to collapse along the pattern of alternating inward and outward folds 28 in the foam body. Drawing the filter portion 14 tightly against the core wire 24, minimizes the diameter of the medical device 10 for insertion. As previously discussed, minimizing the profile of the medical device 10 during insertion reduces the risk of dislodging emboli as the medical device 10 is inserted.

In use, the device 10 expands from the collapsed state to the expanded state, engaging the body vessel with the filter portion 14. In turn, the filter portion 14 expands to open the recess 26 in the conical geometry for capturing emboli during treatment of the stenotic lesion. After the need for such device 10 in the vasculature passes, the device 10 may be retrieved.

Figure 3:
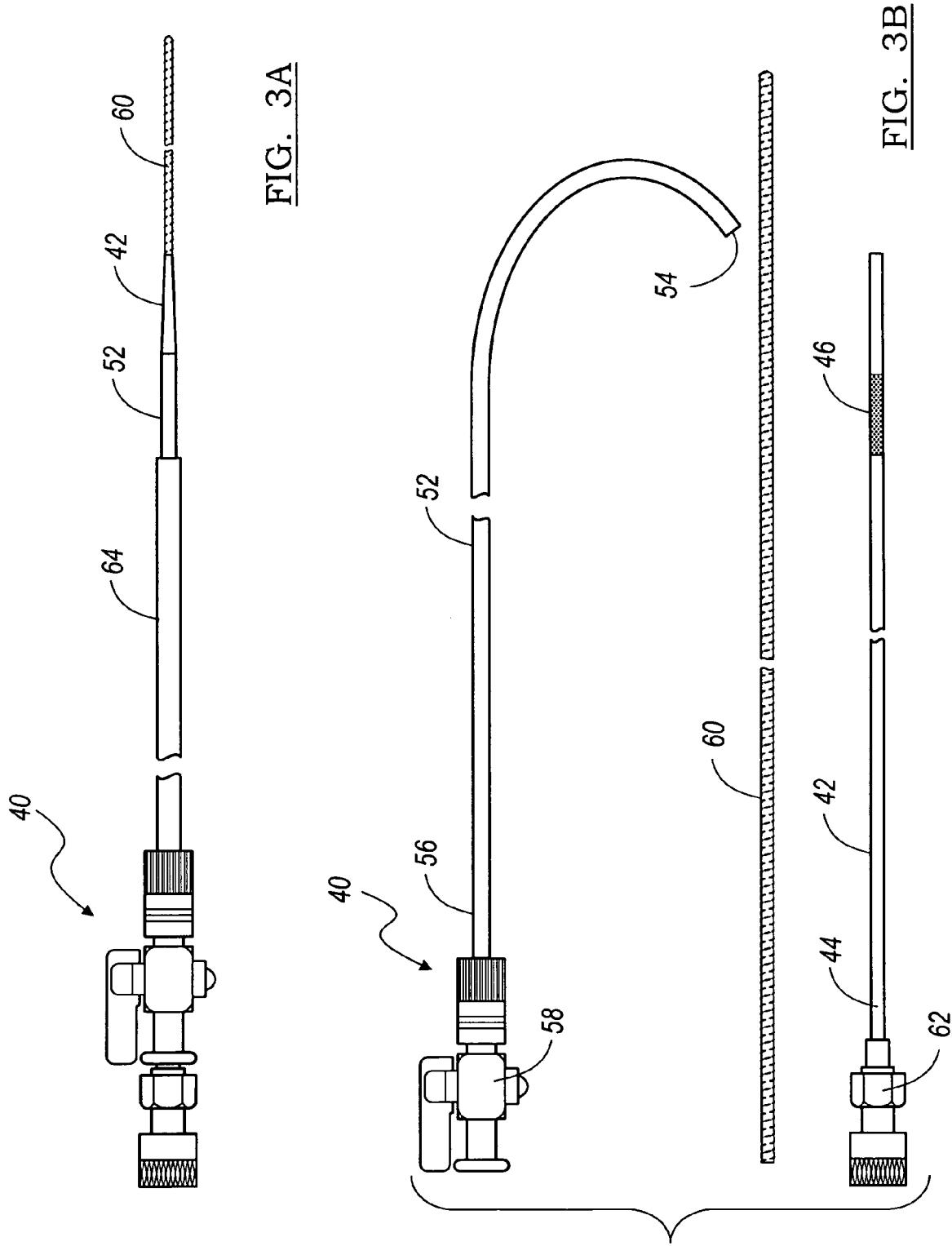

FIGS. 3a and 3b depict an embolic protection assembly 40 for capturing emboli during treatment of a stenotic lesion in a body vessel in accordance with another embodiment of the present invention. As shown, the assembly 40 comprises a balloon catheter 42 having a tubular body 44 and an expandable balloon 46 attached to and in fluid communication with the tubular body 44 for angioplasty at a stenotic lesion. In this embodiment, the assembly 40 comprises the embolic protection device mentioned above. The tubular body 44 is preferably made of soft flexible material such as silicon or any other suitable material. In this embodiment, the balloon catheter 42 includes an outer lumen and an inner lumen. The outer lumen is in fluid communication with the balloon 46 for inflating and deflating the balloon 46. The inner lumen is formed therethrough for percutaneous guidance through the body vessel.

As shown, the assembly 40 further includes an inner catheter 52 having a distal end 54 through which the balloon catheter 42 is disposed for deployment in the body vessel. The inner catheter 52 is preferably made of a soft, flexible material such as silicon or any other suitable material. Generally, the inner catheter 52 further has a proximal end 56 and a plastic adaptor or hub 58 to receive the embolic protection device and balloon catheter 42 to be advanced therethrough. The size of the inner catheter 52 is based on the size of the body vessel in which it percutaneously inserts, and the size of the balloon catheter 42.

As shown, the assembly 40 may also include a wire guide 60 configured to be percutaneously inserted within the vasculature to guide the inner catheter 52 to a location adjacent a stenotic lesion. The wire guide 60 provides the inner catheter 52 (and balloon catheter 42) a path during insertion within the body vessel. The size of the wire guide 60 is based on the inside diameter of the inner catheter 52.

In one embodiment, the balloon catheter 42 has a proximal fluid hub 62 in fluid communication with the balloon 46 via the outer lumen for fluid to be passed therethrough for inflation and deflation of the balloon 46 during treatment of the stenotic lesion.

As shown, the embolic protection device is coaxially disposed through the inner lumen of the balloon catheter 42 prior to treatment of the stenotic lesion in the body vessel. The distal protection device is guided through the inner lumen preferably from the hub 58 and distally beyond the balloon 46 of the balloon catheter 42, exiting from the distal end of the inner or balloon catheter 42 to a location within the vasculature downstream of the stenotic lesion.

In this embodiment, the apparatus further includes a polytetrafluoroethylene (PTFE) introducer sheath 64 for percutaneously introducing the wire guide 60 and the inner catheter 52 in a body vessel. Of course, any other suitable material may be used without falling beyond the scope or spirit of the present invention. The introducer sheath 64 may have any suitable size, e.g., between about three-french to eight-french. The introducer serves to allow the inner and balloon catheters 42 to be percutaneously inserted to a desired location in the body vessel. The introducer sheath 64 receives the inner catheter 52 and provides stability to the inner catheter at a desired location of the body vessel. For example, the introducer sheath 64 is held stationary within a common visceral artery, and adds stability to the inner catheter 52, as the inner catheter 52 is advanced through the introducer sheath 64 to a dilatation area in the vasculature.

When the distal end 54 of the inner catheter 52 is at a location downstream of the dilatation area in the body vessel, the balloon catheter 42 is inserted therethrough to the dilatation area. The device 10 is then loaded at the proximal end of the balloon catheter 42 and is advanced through the inner lumen thereof for deployment through its distal end. In this embodiment, the proximal stem is used to mechanically advance or push the device 10 through the catheter.

Figure 4:
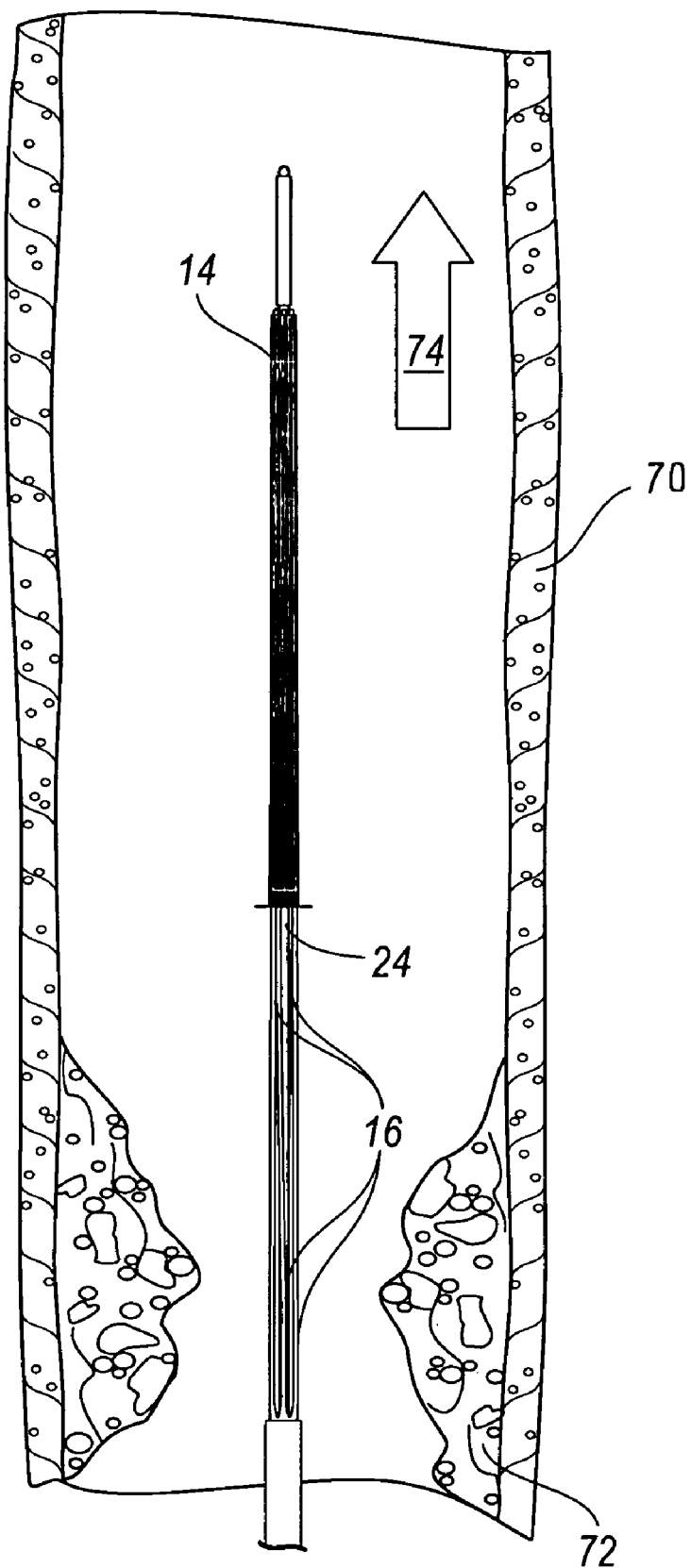
FIG. 4 is a sectional view of a blood vessel illustrating insertion of the medical device of FIG. 1 in the collapsed state.

Now referring to FIG. 4, a cutaway view of a vessel 70 is provided illustrating insertion of the medical device 10. The medical device 10 is inserted with the basket 12 in a collapsed state, allowing the medical device 10 to navigate through the narrow opening formed by the stenosed area 72. Accordingly, during insertion, the profile of the medical device 10 should be minimized. As such, the core wire 24 is moved distally relative to the struts 16 drawing the struts 16 and the filter portion 14 tightly against the core wire 24, thereby forming a collapsed state. The medical device 10 is inserted into the vessel 70 past the stenosis 72 as denoted by the distally pointing arrow 74.

Figure 5:
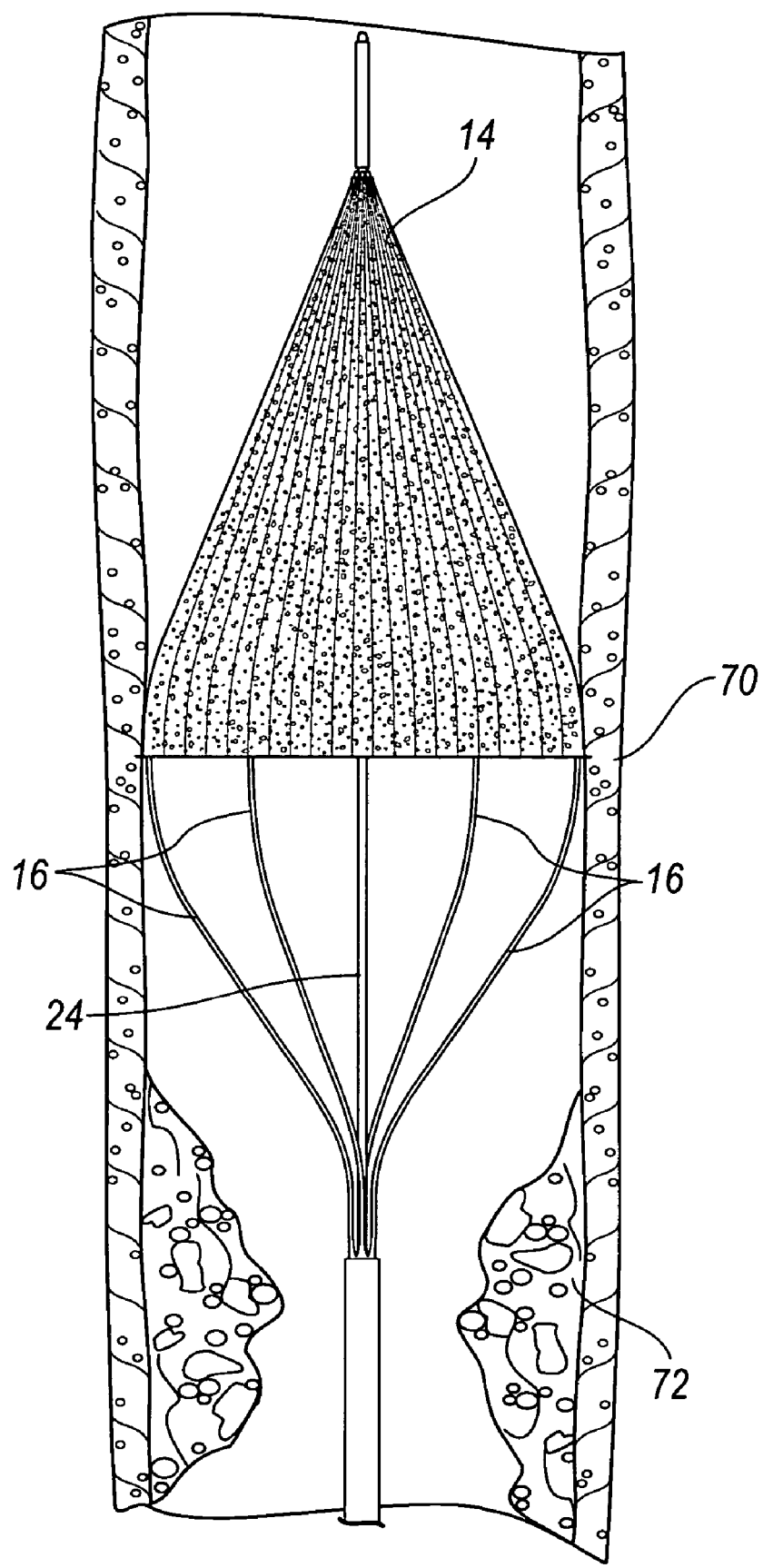
FIG. 5 is a sectional view of the blood vessel illustrating the medical device of FIG. 1 in a fully deployed state.

Once the basket portion 12 of the medical device 10 is located distal the stenosis 72, the basket portion 12 can be expanded against the inner wall of the blood vessel 70 as shown in FIG. 5. As previously discussed, the filter portion 14 may also be made of a shape memory material such that the filter portion 14 has two defined geometries. For example, the mesh material may be made of a shape memory alloy so that the foam body is biased into a collapsed state at a first temperature. The first temperature being controlled, for example, by fluid flowing through a guiding catheter 16 across the medical device 10. At a second temperature, such as the ambient temperature inside the vessel 70, the filter portion 14 is biased into a proximally facing concave geometry.

Figure 6:
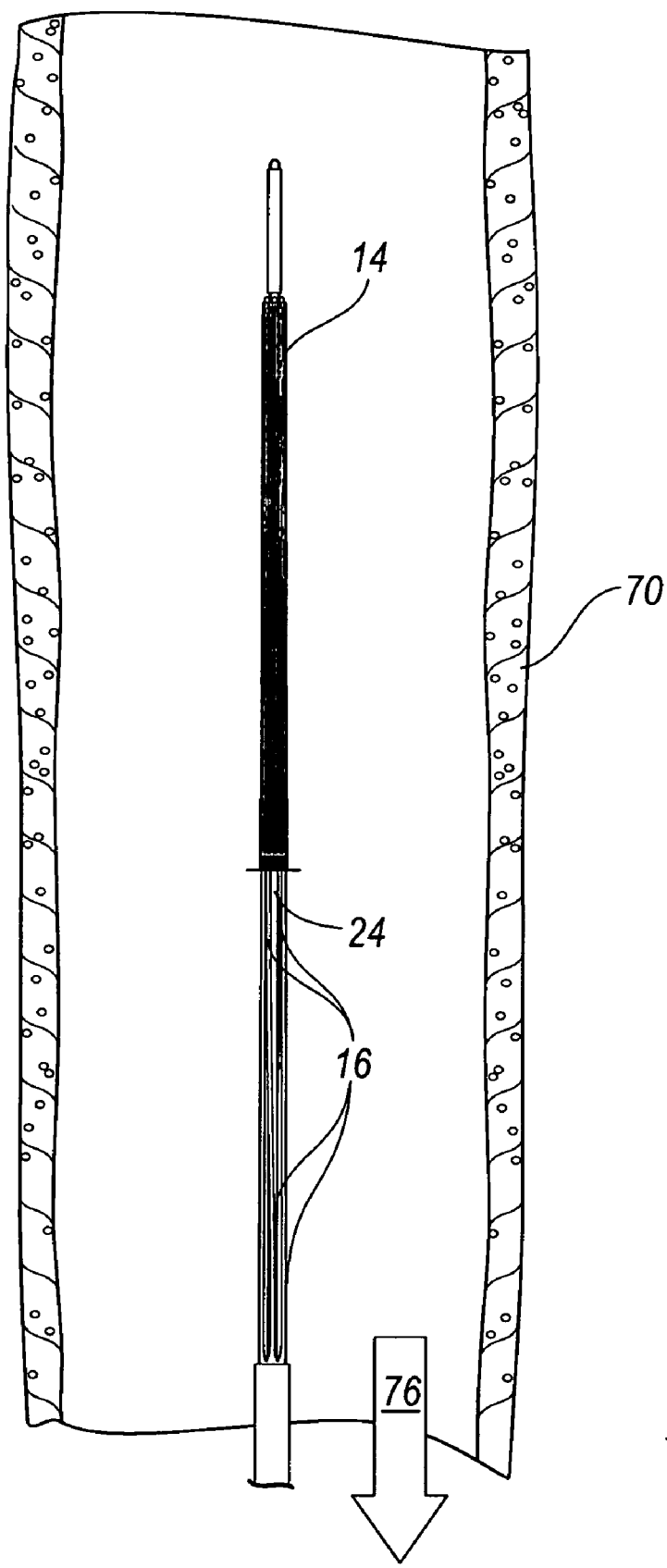
FIG. 6 is a sectional view of the blood vessel illustrating removal of the medical device from the vessel.

In the expanded state, the struts 16 and filter portion 14 provide a radial force against the inner wall of the vessel 70. The radial force eliminates gaps between the filter portion 14 and the vessel 70 forcing embolic material that is released from the stenosis 72 to be trapped downstream in the recess 26 of the filter portion 14. After a procedure is performed on the stenosis 72, the core wire 24 is moved distally relative to the struts 16 to collapse the struts 16 and filter portion 14 tightly against the core wire 24, as shown in FIG. 6. In the collapsed state, the emboli are trapped within the filter portion 14 and a catheter is slid over the medical device 10. The medical device 10 in the collapsed state, may then be removed proximally as denoted by proximally pointing arrow 76.

Figure 7:
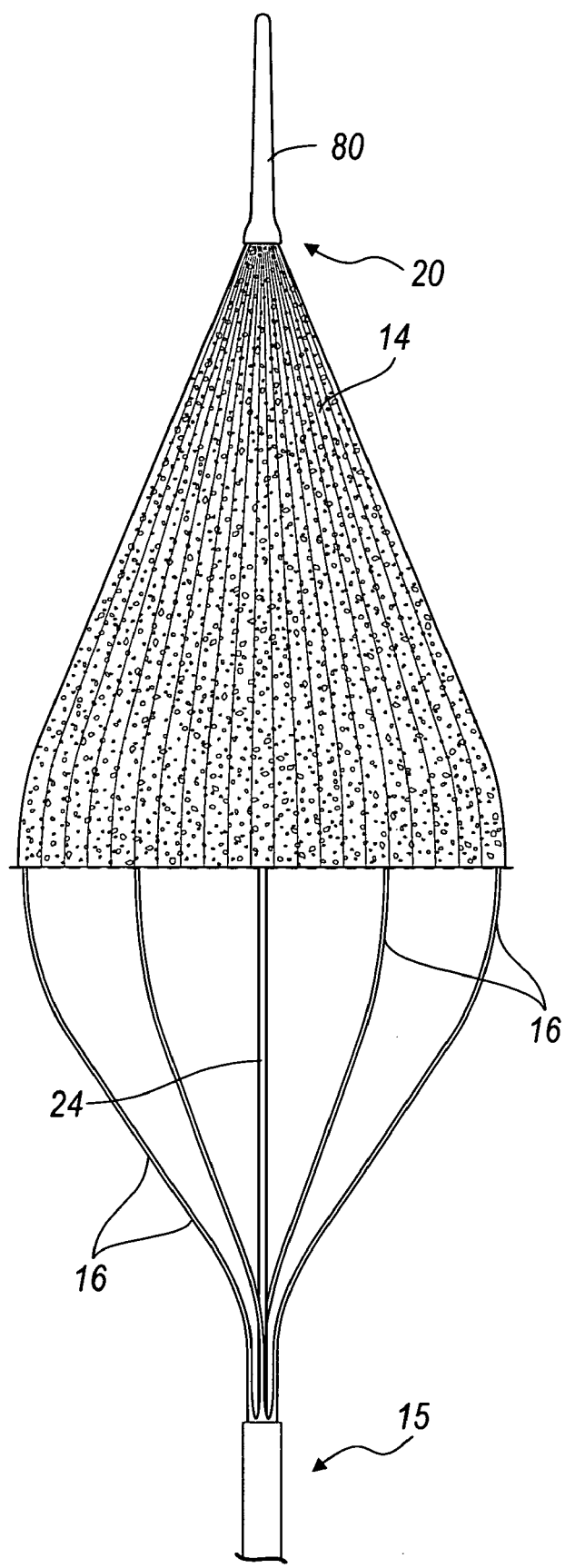
FIG. 7 is a side view of another embodiment of the present invention including a floppy tip.

Now referring to FIG. 7, the medical device 10 may include a floppy tip 80 located distal the second end 20 of the basket 12 to provide additional guidance during insertion. The floppy tip 80 may extend from the second end 20 and may include a hydrophilic or other lubricious coating to facilitate easy advancement of the medical device to and through the stenosed region of the blood vessel during insertion. The floppy tip 80 is attached to the second end 20, for example by adhesive bonding, and may be made of nylon, polymeric material, silicone, Teflon, or other commonly known material without falling beyond the scope or spirit of the present invention. The flexibility provided by the floppy tip 80, aids in advancement of the medical device through the vessel while minimizing any trauma caused during the advancement.

Figure 8:
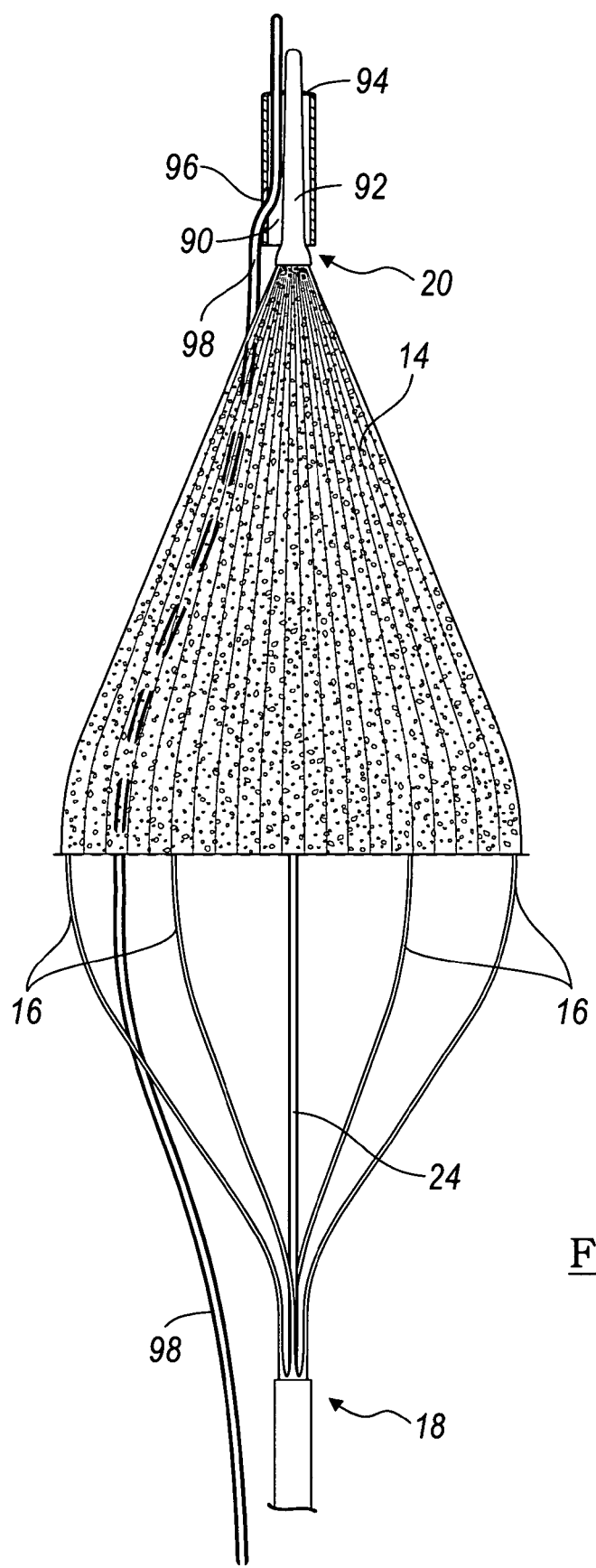
FIG. 8 is a side view of yet another embodiment of the present invention including a guide wire adapter.

Now referring to FIG. 8, another embodiment of a medical device in accordance with the present invention is provided. A tubular member 90 may be located on a tip 92 or in lieu of the tip extending distally from the second end 20 of the basket portion 12. The tubular member 90 may be made of nylon, polymeric material, Teflon, superelastic metal or other commonly known material without falling beyond the scope or spirit of the present invention. The tubular member 90 may include a first opening 94 and a second opening 96 such that a wire guide 98 may extend through the first and second opening 94, 96 of the tubular member 90. Accordingly, the tubular member 90 allows the medical device 10 to be guided along the wire guide 98 or alternatively allowing the wire guide 98 to be advanced together with the medical device 10 during insertion.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

We claim:

1. An embolic protection device for use in a vessel, the embolic protection device comprising:
   a filter portion including a porous foam body comprised of a shape memory alloy foam, pores of the porous foam body being sized to allow blood to flow through the foam body; and
   a plurality of struts attached to the filter portion and extending proximally therefrom, the filter portion and the plurality of struts forming a basket, where the basket is configured to have an expanded and collapsed state;
   wherein the foam body has a generally conical geometry and wherein the struts are radially spaced around the circumference of the generally conical geometry; and a plurality of folds in the generally conical geometry, each fold extending radially from an apex of the generally conical geometry and along a side of the generally conical geometry.

2. The embolic protection device according to claim 1, wherein the filter portion is comprised of a Nitinol foam.

3. The embolic protection device according to claim 1, further comprising a core wire attached to a distal end of the filter portion and extending proximally through the basket.

4. The embolic protection device according to claim 1, wherein the basket is biased into an expanded state.

5. The embolic protection device according to claim 1, wherein the filter portion includes a recess configured to trap emboli.

6. The embolic protection device according to claim 1, wherein the plurality of folds form an alternating pattern of inward and outward folds periodically spaced around a circumference of the generally conical geometry.

7. The embolic protection device according to claim 1, further comprising a floppy tip attached to the distal end of the basket.

8. The embolic protection device according to claim 1, further comprising a tubular portion attached to the distal end of the basket, the tubular portion being configured to receive a wire guide through the tubular portion.

9. An embolic protection device according to claim 1, wherein the pores are between about 80 and 100 micrometers.

10. An embolic protection device for use in a vessel, the embolic protection device comprising:
    a filter portion including a porous Nitinol foam body having a conical geometry, pores of the porous Nitinol foam body being sized to allow blood to flow through the foam body;
    a plurality of struts attached to the filter portion and extending proximally therefrom, the filter portion and the plurality of struts forming a basket, where the basket is configured to have an expanded and collapsed state; and
    a plurality of folds in the conical geometry, the plurality of folds extending radially from an apex of the conical geometry and along a side of the conical geometry, wherein the plurality of folds form an alternating pattern of inward and outward folds periodically spaced around a circumference of the conical geometry.

11. The embolic protection device according to claim 10, wherein the basket is biased into an expanded state.

12. The embolic protection device according to claim 10, wherein the struts are radially spaced around the circumference of the conical geometry.

13. The embolic protection device according to claim 10, wherein the filter portion includes a recess configured to trap emboli.

14. The embolic protection device according to claim 13, wherein the recess has a generally conical geometry.

15. An embolic protection device according to claim 10, wherein the pores are between about 80 and 100 micrometers.

16. An embolic protection device for use in a vessel, the embolic protection device comprising:
    a filter portion including a porous foam body, the foam body having a generally conical geometry including a plurality of folds, each fold extending radially from an apex of the generally conical geometry and along a side of the generally conical geometry; and
    a plurality of struts attached to the filter portion and extending proximally therefrom, the filter portion and the plurality of struts forming a basket, where the basket is configured to have an expanded and collapsed state.

* * * * *